(12) United States Patent
Jeffries et al.

(10) Patent No.: US 10,549,022 B2
(45) Date of Patent: Feb. 4, 2020

(54) EXTRACORPOREAL GAS EXCHANGE DEVICES, SYSTEMS AND METHODS

(71) Applicant: University of Pittsburgh—Of the Commonwealth System of Higher Education, Pittsburgh, PA (US)

(72) Inventors: Richard Garrett Jeffries, Philadelphia, PA (US); William J. Federspiel, Pittsburgh, PA (US); Brian Joseph Frankowski, Imperial, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 163 days.

(21) Appl. No.: 15/542,532

(22) PCT Filed: Jan. 20, 2016

(86) PCT No.: PCT/US2016/014029
§ 371 (c)(1),
(2) Date: Jul. 10, 2017

(87) PCT Pub. No.: WO2016/118567
PCT Pub. Date: Jul. 28, 2016

(65) Prior Publication Data
US 2018/0264184 A1    Sep. 20, 2018

Related U.S. Application Data

(60) Provisional application No. 62/105,467, filed on Jan. 20, 2015.

(51) Int. Cl.
*A61M 1/26* (2006.01)
*A61M 1/16* (2006.01)
*A61M 1/10* (2006.01)

(52) U.S. Cl.
CPC .......... *A61M 1/262* (2014.02); *A61M 1/1006* (2014.02); *A61M 1/1698* (2013.01);
(Continued)

(58) Field of Classification Search
CPC .... A61M 1/262; A61M 1/1006; A61M 1/267; A61M 1/1678; A61M 1/1698;
(Continued)

(56) References Cited

U.S. PATENT DOCUMENTS 6,503,450 B1 * 1/2003 Afzal .................. A61M 1/1698
422/45
7,763,097 B2   7/2010 Federspiel
(Continued)

FOREIGN PATENT DOCUMENTS

EP    2689792 A1    1/2014
WO   WO2016118567   7/2016

*Primary Examiner* — Philip R Wiest
(74) *Attorney, Agent, or Firm* — Bartony & Associates, LLC

(57) ABSTRACT

An extracorporeal gas exchange device includes a housing, a rigid shaft rotatable within the housing, a plurality of agitation mechanisms positioned on the rigid shaft, and a plurality of hollow gas permeable fibers adapted to permit diffusion of gas between fluid flowing within the housing and an interior of the plurality of hollow gas permeable fibers. The plurality of hollow gas permeable fibers are positioned radially outward from the plurality of agitation mechanisms. The rotational speed of the rigid shaft is adjustable independent of the flow rate of fluid through the housing.

18 Claims, 14 Drawing Sheets

(52) U.S. Cl.
CPC ............ *A61M 1/267* (2014.02); *A61M 1/101* (2013.01); *A61M 1/1086* (2013.01)

(58) Field of Classification Search
CPC ...... A61M 1/101; A61M 1/1086; A61M 1/26; A61M 1/265
See application file for complete search history.

(56) References Cited

U.S. PATENT DOCUMENTS

| | | |
|---|---|---|
| 7,927,544 B2 | 4/2011 | Federspiel |
| 8,043,411 B2 | 10/2011 | Federspiel |
| 8,585,969 B2 | 11/2013 | Maianti |
| 8,647,569 B1 | 2/2014 | Federspiel |
| 8,734,382 B2 | 5/2014 | Frankowski |
| 2007/0249888 A1 | 10/2007 | Wu |
| 2010/0331767 A1* | 12/2010 | Frankowski ........ A61M 1/1678 604/26 |
| 2014/0228741 A1 | 8/2014 | Frankowski |

* cited by examiner

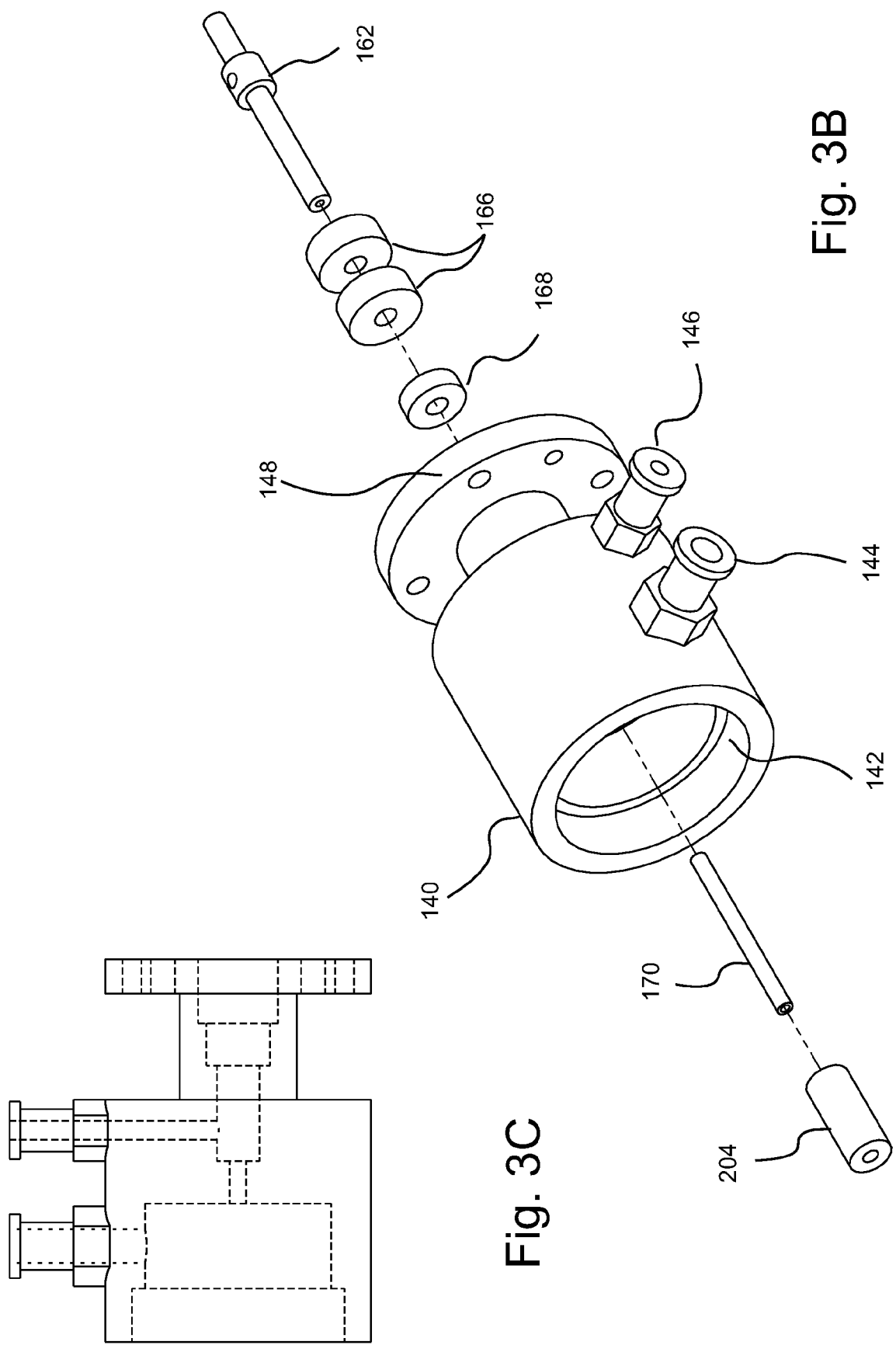

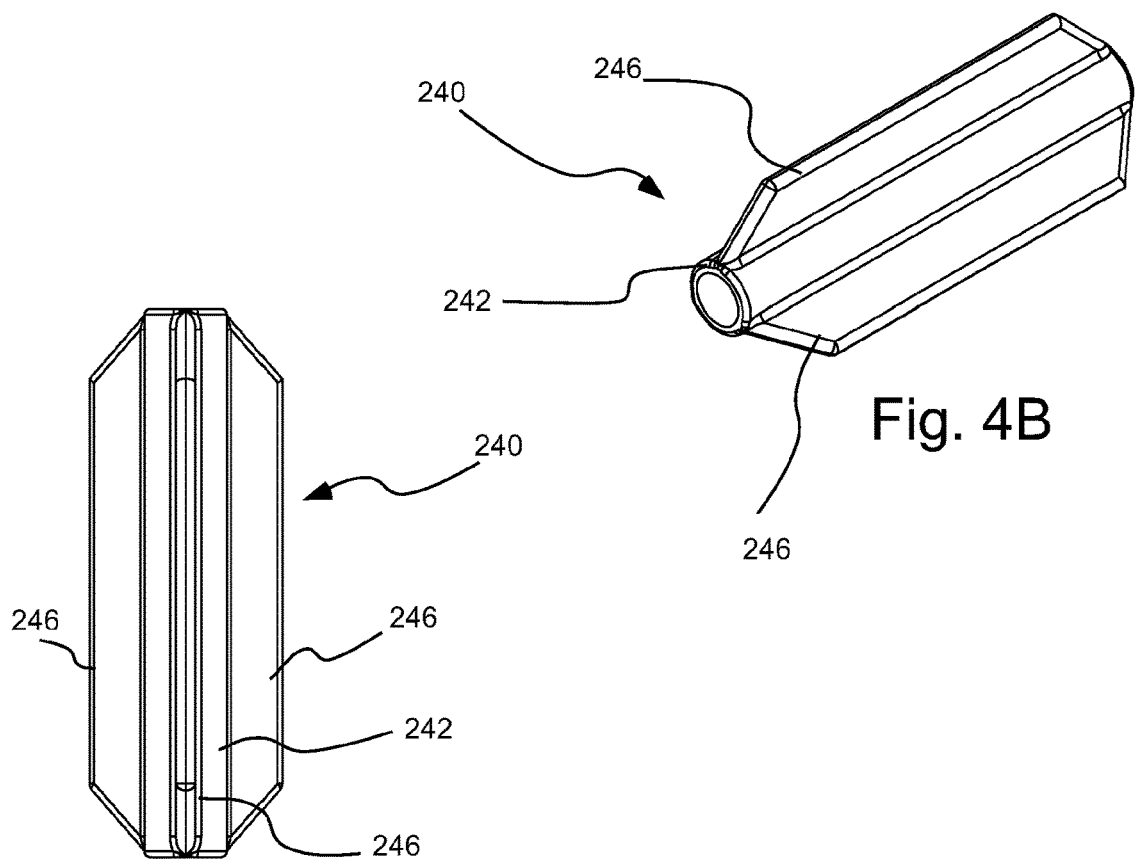
Fig. 4B
Fig. 4A
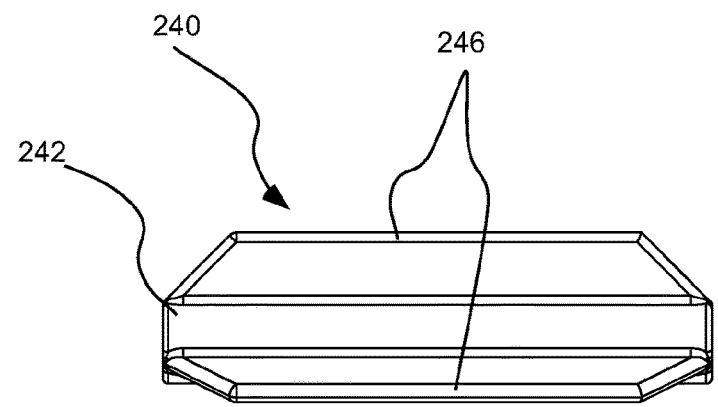
Fig. 4C
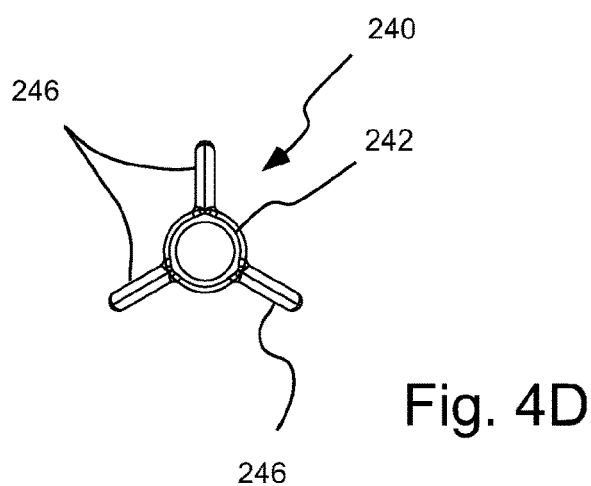
Fig. 4D

EXTRACORPOREAL GAS EXCHANGE DEVICES, SYSTEMS AND METHODS

CROSS-REFERENCE TO RELATED APPLICATIONS

This application claims benefit of U.S. Provisional Patent Application Ser. No. 62/105,467, filed Jan. 20, 2015, the disclosure of which is incorporated herein by reference.

GOVERNMENTAL INTEREST

This invention was made with government support under grants numbers HL070051 and HL117637 awarded by the National Institutes of Health. The government has certain rights in this invention.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Lung disease is one of the major healthcare problems present in the United States today. Respiratory failure is a syndrome in which the respiratory system fails in one or both of its gas exchange functions: oxygenation and carbon dioxide elimination. In practice, respiratory failure may be classified as either hypoxemic or hypercapnic. Hypoxemic respiratory failure, which is sometime referred to as type I respiratory failure, is characterized by an arterial oxygen tension (Pa $O_2$) lower than 60 mm Hg with a normal or low arterial carbon dioxide ($CO_2$) tension (Pa $CO_2$). Hypoxemic respiratory failure is the most common form of respiratory failure. It may be associated with nearly all acute diseases of the lung. Hypercapnic respiratory failure, which is sometimes referred to as type II respiratory failure, is characterized by a $PaCO_2$ higher than 50 mm Hg. Hypoxemia is also common in patients with hypercapnic respiratory failure who are breathing room air. Hypercapnic respiratory failure is, for example, commonly associated with severe airway disorders such as asthma, chronic obstructive pulmonary disease or COPD, and acute respiratory distress syndrome or ARDS.

Extracorporeal support systems are under development to effect carbon dioxide removal. However, clinical adaptation of developing extracorporeal carbon dioxide removal systems ($ECCO_2R$) for management of hypercapnic respiratory failure has been hindered by the high blood flow rates necessary to provide adequate support. The high blood flow rates require a larger cannula inserted into the patient and increases the invasiveness of the procedure as a result.

SUMMARY

In one aspect, an extracorporeal gas exchange device includes a housing, a rigid shaft rotatable within the housing, at least one agitation mechanism positioned on the rigid shaft, and a plurality of hollow gas permeable fibers adapted to permit diffusion of gas between fluid flowing within the housing and an interior of the hollow fibers. The plurality of hollow fibers are positioned radially outward from the agitation mechanism. The rotational speed of the rigid shaft may, for example, be adjustable independent of the flow rate of fluid through the housing.

The extracorporeal gas exchange device may, for example, include a sweep gas inlet in fluid connection with an inlet end of the plurality of hollow gas fibers, a sweep gas outlet in fluid connection with an outlet end of the plurality of hollow gas fibers, a fluid inlet, and a fluid outlet. The fluid inlet and the fluid outlet are isolated from fluid connection with the sweep gas inlet and the sweep gas outlet.

In a number of embodiments, the extracorporeal gas exchange includes a plurality of agitation mechanisms (for example, 3 to 30 or 3 to 15 agitation mechanism) positioned on the rigid shaft. The plurality of agitation mechanisms may for example, include a plurality of impellers in spaced positions on the rigid shaft. The plurality of impellers (or other agitation mechanisms) may, for example, be generally evenly spaced on the rigid shaft. Each of the plurality of impellers may, for example, include a plurality of vanes extending along the length thereof and extending radially outward therefrom. In a number of embodiment, each of the vanes are curved. The agitation mechanism(s) may, for example, be adjacent the plurality of hollow gas permeable fibers without an intervening component.

The fluid inlet may, for example, be adapted to be placed in fluid connection with a patient and the fluid may be blood (or a blood-derived fluid; blood and blood-derived fluids are referred to herein collectively as blood). A sweep gas placed in fluid connection with the sweep gas inlet may, for example, be adapted to remove carbon dioxide from the blood. The sweep gas may, for example, include oxygen.

In a number of embodiments hereof, extracorporeal gas exchange devices hereof are adapted to have a flow rate of blood through the housing in the range of approximately 200 to approximately 500 or approximately 200 to approximately 400 mL/min.

In another aspect an extracorporeal gas exchange device includes a housing, a rigid shaft rotatable within the housing, at least one agitation mechanism positioned on the rigid shaft, and a plurality of hollow gas permeable fibers adapted to permit diffusion of gas between fluid flowing within the housing and an interior of the hollow fibers, wherein the plurality of hollow fibers are positioned radially outward from the agitation mechanism. The agitation mechanism may, for example, be positioned adjacent the plurality of hollow gas permeable fibers without an intervening component. The rotational speed of the rigid shaft may, for example, be adjustable independent of the flow rate of fluid through the housing.

In a further aspect, an extracorporeal gas exchange device includes a housing, a shaft rotatable within the housing, at least one agitation mechanism positioned on the shaft, and a plurality of hollow gas permeable fibers adapted to permit diffusion of gas between fluid flowing within the housing and an interior of the hollow fibers. The plurality of hollow fibers are positioned radially outward from the agitation mechanism. In a number of embodiment, the plurality of hollow fibers are oriented generally parallel to the orientation of the rigid shaft (that is, within 5, 2 degrees or 1 degree of parallel). The rotational speed of the shaft is adjustable independent of the flow rate of fluid through the housing.

In another aspect, a system includes at least one pump device adapted to effect fluid flow, at least one dialysis system in fluid connection with the at least one pump device; and at least one extracorporeal gas exchange device hereof in fluid connection with the at least one pump device and the at least one dialysis system.

The present devices, systems, methods and compositions, along with the attributes and attendant advantages thereof, will best be appreciated and understood in view of the following detailed description taken in conjunction with the accompanying drawings.

BRIEF DESCRIPTION OF THE DRAWINGS

FIG. 3B illustrates an enlarged perspective, exploded or disassembled view a portion of the device of FIG. 1A including a second housing end member thereof.

FIG. 3C illustrates a hidden line view of the second housing end member of the device of FIG. 1A.

FIG. 4A illustrates a top view of an embodiment of an impeller or rotor for use in the device of FIG. 1A.

FIG. 4B illustrates a perspective view of the impeller of FIG. 4A.

FIG. 4C illustrates a side view of the impeller of FIG. 4A.

FIG. 4D illustrates a front view of the impeller of FIG. 4A.

DETAILED DESCRIPTION

Figure 1A:
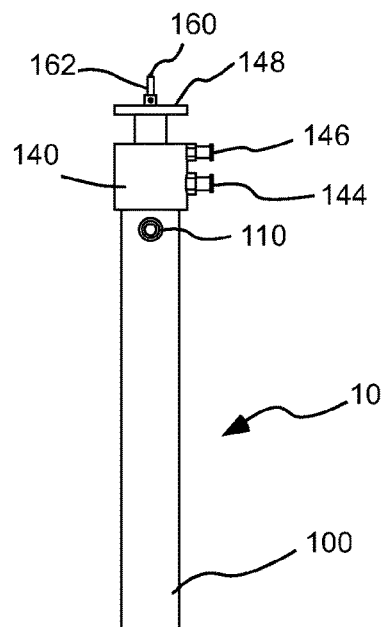
FIG. 1A illustrates a side view of an embodiment of an extracorporeal $CO_2$ removal device hereof.
Figure 1B:
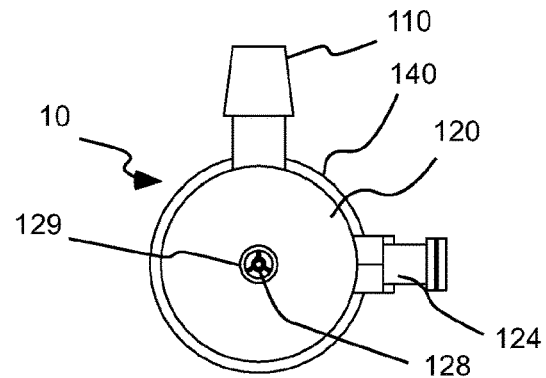
FIG. 1B illustrates a front view of the device of FIG. 1A.
Figure 1C:
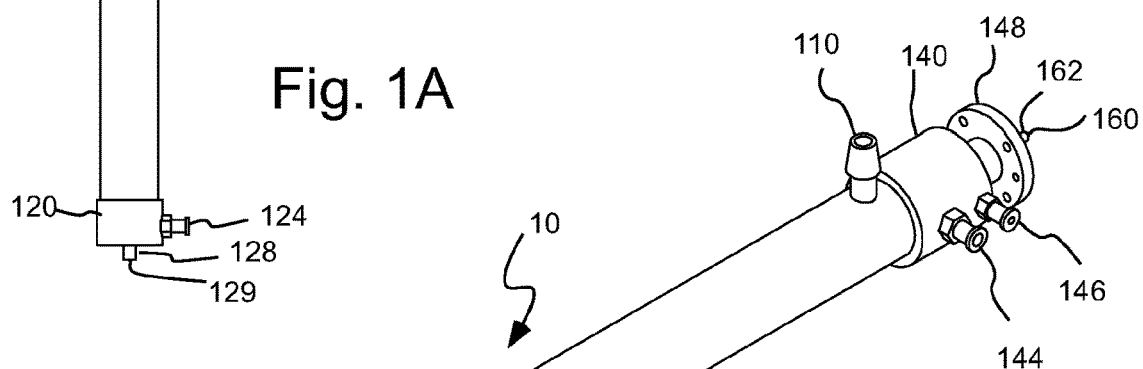
FIG. 1C illustrates a perspective view of the device of FIG. 1A.
Figure 1D:
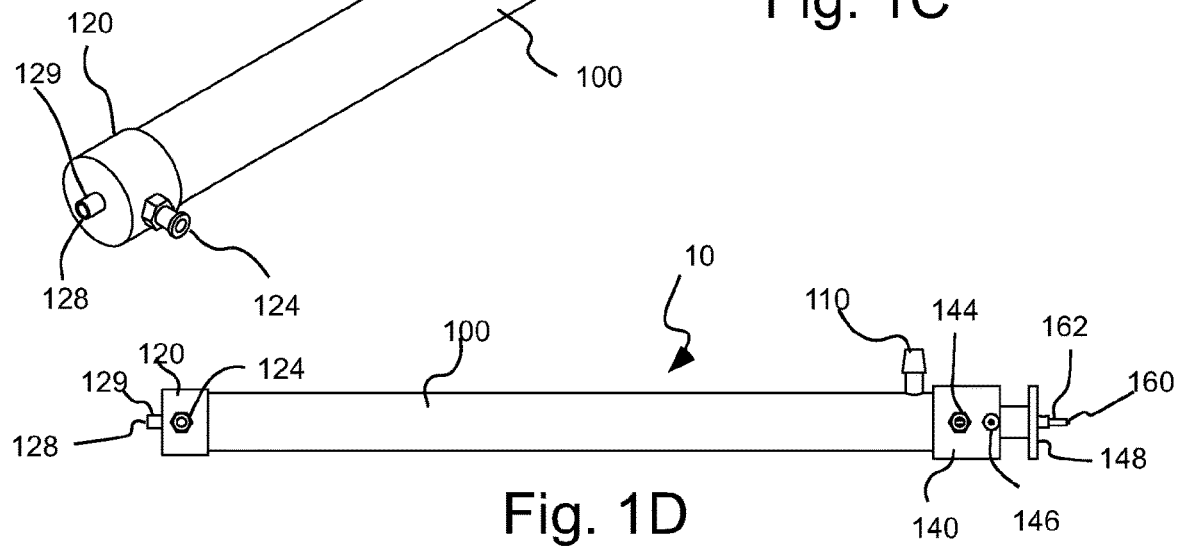
FIG. 1D illustrates a top view of the device of FIG. 1A.

It will be readily understood that the components of the embodiments, as generally described and illustrated in the figures herein, may be arranged and designed in a wide variety of different configurations in addition to the described representative embodiments. Thus, the following more detailed description of the representative embodiments, as illustrated in the figures, is not intended to limit the scope of the embodiments, as claimed, but is merely illustrative of representative embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "an impeller" includes a plurality of such impellers and equivalents thereof known to those skilled in the art, and so forth, and reference to "the impeller" is a reference to one or more such impellers and equivalents thereof known to those skilled in the art, and so forth. Recitation of ranges of values herein are merely intended to serve as a shorthand method of referring individually to each separate value falling within the range. Unless otherwise indicated herein, and each separate value, as well as intermediate ranges, are incorporated into the specification as if individually recited herein. All methods described herein can be performed in any suitable order unless otherwise indicated herein or otherwise clearly contraindicated by the text. Unless the context clearly dictates otherwise, use of the terms "approximately", "about" and similar terms refer to a value within 10% of the stated valued.

In a number of embodiments of devices, cartridges, or systems hereof, an array of rotating impellers or rotors facilitates highly efficient gas exchange in, for example, an artificial lung device and allows operation at significantly lower blood flow rates than existing technology. The blood flow rates used in systems hereof may, for example, approximate or match those used in hemodialysis (for example, approximately 250 ml/min). The ability of devices, systems and methods hereof to achieve clinically relevant levels of $CO_2$ removal at flow rates typical used in renal hemodialysis is unprecedented. The relatively low flow rates through devices hereof provide, for example, for simplified cannulation strategies (for example, the use of smaller and/or less invasive cannula) and potential integration of devices and systems hereof into existing renal dialysis circuits.

In a number of embodiments hereof, blood pumped from the body to an extracorporeal device, system, or cartridge hereof is recirculated in and out of a fiber membrane bundle (a plurality of hollow fiber membranes) as a result of, for example, rotor- or impeller-generated circulation/pumping before exiting the device and returning to the body. Intimate interactions between rotating impellers of the devices hereof and the surrounding hollow fiber membranes (HFMs) (see, for example, FIG. 2B) generates an active mixing effect. As used herein, the term active mixing refers generally to generating flow past the surface of hollow fiber membranes, preferably perpendicular thereto, at a higher velocity than would exist if the velocity arose only from the bulk blood flow through the device. Because the size of the diffusional boundary layer scales roughly as the inverse square root of velocity, the diffusional boundary layer is reduced as a result. Active mixing provides a method of enhancing gas transfer capabilities in, for example, hollow fiber membrane (HFM) based artificial lung devices hereof. High fluid velocities at the gas exchange surfaces generated by impeller pumping, which diminishes the thickness of the diffusive boundary layer at the fiber surface. Convective delivery and removal of blood gases from the membrane surface is improved, enhancing gas transfer efficiency. In a number of embodiments hereof, impellers which are used to create active mixing pump fluid only in the radial direction, generally perpendicular to the orientation of the HFM and to bulk fluid flow through the device, and therefore have no or substantially no effect on circuit blood flow rate. One or more pumping or pressurizing mechanisms or devices, separately controllable from the impellers, is/are used to effect bulk fluid flow through the device. As a result, the level of active mixing (and associated gas exchange) is controllable independently of circuit flow rate (or control of the pressurizing mechanism(s) which causes flow through the circuit or system).

As described above, rotating impellers within a HFM bundle generate an active mixing effect that enhances gas exchange capabilities, allowing operation of the device at lower blood flow rates than comparably sized devices. The impellers hereof pump (that is, impart motion to the fluid flow) in the radial direction (generally perpendicular to bulk flow) without a significant effect on bulk flow, and therefore do not contribute to or inhibit blood flow through the device, allowing impeller speed (i.e. level of active mixing and associated improvement in gas exchange) to be controlled independently of device blood flow. This feature improves the versatility of the devices and system hereof, allowing such devices or systems to be operated in a stand-alone circuit or spliced/integrated into an existing blood circuit (for example, a renal hemodialysis flow circuit).

In a number of embodiments, extracorporeal gas exchange (for example, $CO_2$ removal) devices hereof create active mixing through rotation of impellers on a rigid driveshaft. The driveshaft may, for example, be suspended concentrically within a hollow fiber membrane bundle. As described above, the impellers may, for example, generate flow substantially only or only in the radial direction, thereby contributing to substantially no or no change in total flow rate through the device (that is, bulk flow rate from the inlet to the outlet of the device). In addition to the ability of operation at blood flow rates similar to renal hemodialysis, the devices hereof may be spliced directly into existing dialysis circuitry with minimal disturbance in that system's normal operation, or be used with dialysis pump circuits.

The rigid impeller driveshaft of the devices hereof assists in preventing impeller blade contact with any surrounding device components. The rigid driveshaft substantially reduces or eliminates the potential for blood cell trauma resulting from impeller vane/blade contact with static surfaces (thereby, significantly improving hemocompatibility). Compared to flexible shaft technology, a rigid shaft provides for significantly improved impeller durability because the impeller surface wear is greatly reduced. Therefore, in a number of embodiments of devices hereof, protective coils (or other support member) surrounding the impeller may be omitted. In that regard, the agitation mechanism used in the devices hereof (for example, impeller vanes) may be directly adjacent to the hollow fiber bundle without intervening components. A coil or support may be used adjacent the inner wall of the hollow fiber bundle to assist in maintaining a well-formed annular configuration of the hollow fiber bundle. However, such a coil or support need only be sufficiently robust to support the annular fiber bundle and need not operate to protect the fiber bundle from contact with the agitation mechanisms supported on the rotating rigid shaft.

An embodiment of a device 10 hereof and components thereof are illustrated in FIGS. 1A through 4D. As, for example, illustrated in FIG. 1A through 3A, device 10 includes a housing having an extending housing section or body 100 which may, for example, be formed from a polymeric material or materials such as an acrylic polymer. In a number of embodiments, a blood outlet port 110 is formed in housing body 100. In the illustrated embodiment, the housing further includes a first end member 120 connected to a first end of housing body 100. First housing end member 120 includes a sweep gas outlet port 124 and a blood inlet port 128. Sweep gas outlet port 124 may, for example, include a luer lock connector or luer connector as known in the medical arts. In the illustrated embodiment, a second housing end member 140 is connected to a second end of housing body 100. In the illustrated embodiment, the housing further includes a second housing end member 140, which includes a sweep gas inlet port 144 and a saline port 146. Each of sweep gas inlet port 144 and saline port 146 may, for example, include a luer lock connector or luer connector as known in the medical arts.

Figure 2A:
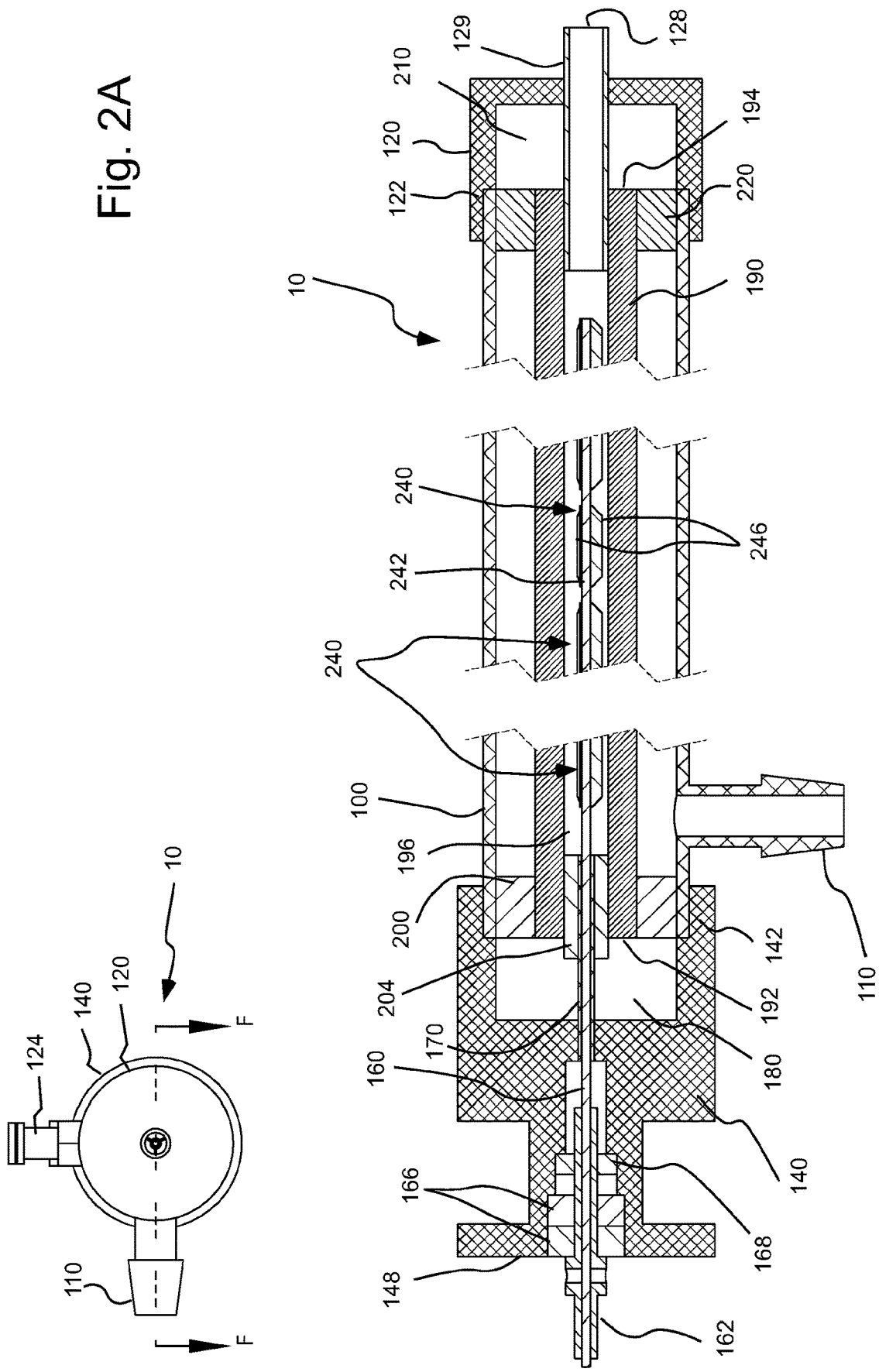
FIG. 2A illustrates a cross-sectional view of the device of FIG. 1A along plane F-F.
Figure 2B:
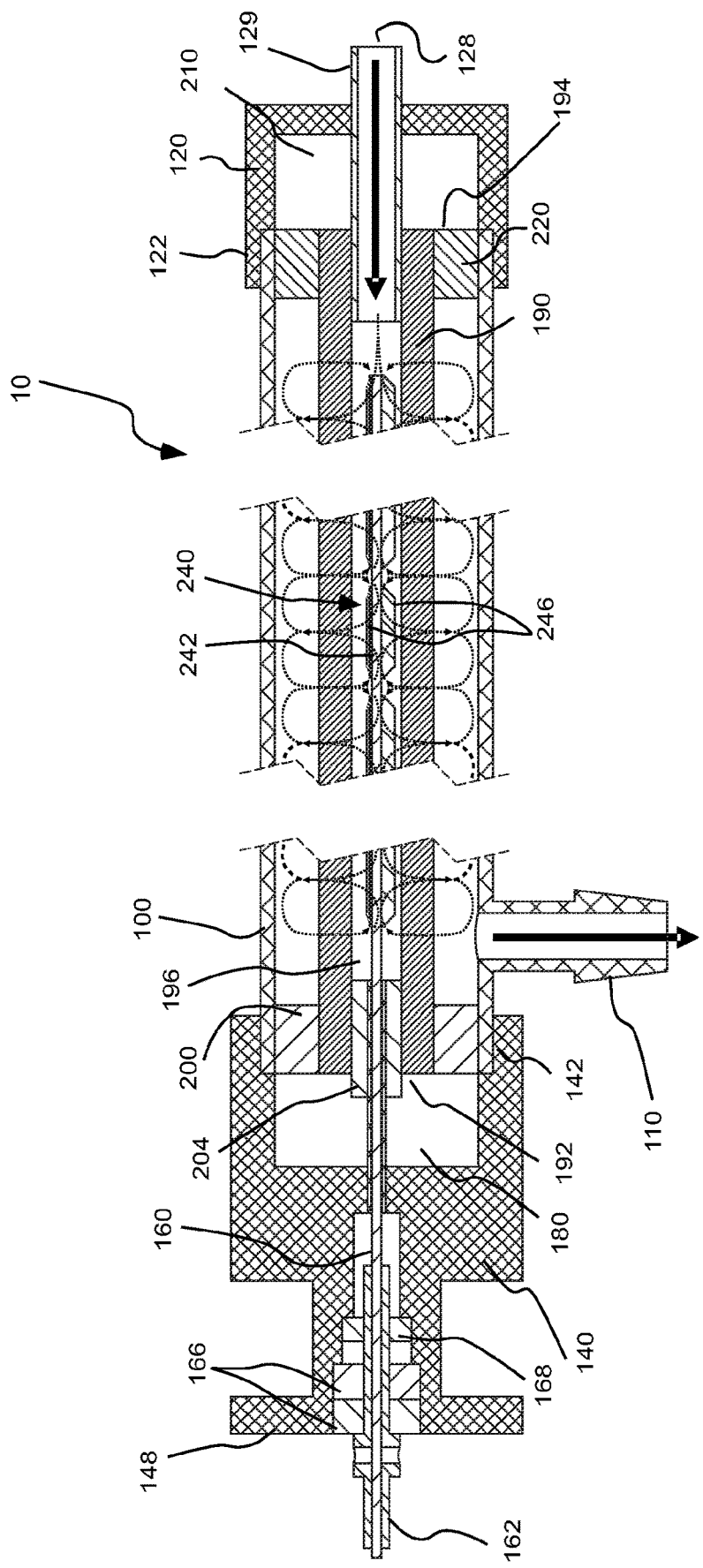
FIG. 2B illustrates a cross-sectional view of the device of FIG. 1A showing idealized flow lines of blood flow through the device including active mixing induced by impellers.
Figure 2C:
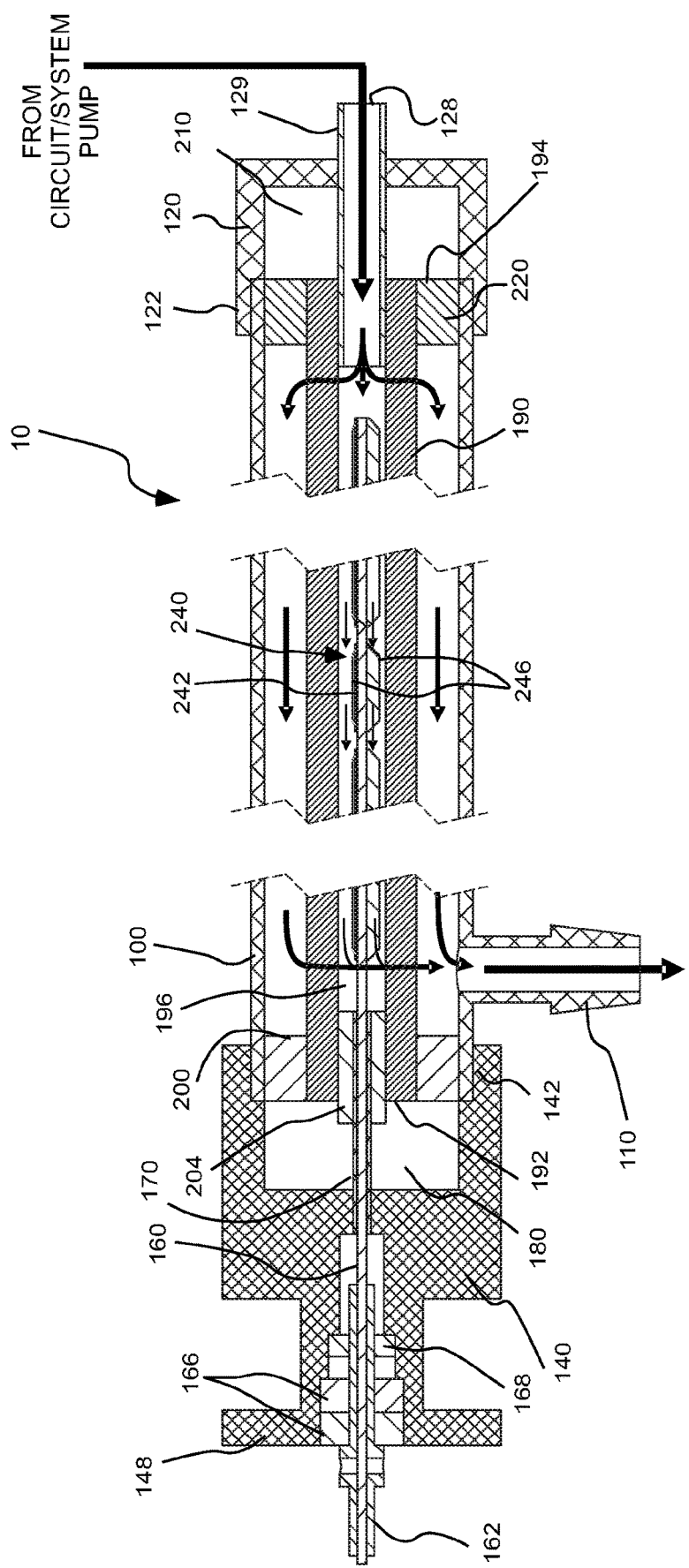
FIG. 2C illustrates a cross-sectional view of the device of FIG. 1A showing idealized flow lines of bulk flow blood of blood through the device without active mixing induced by impellers.
Figure 2D:
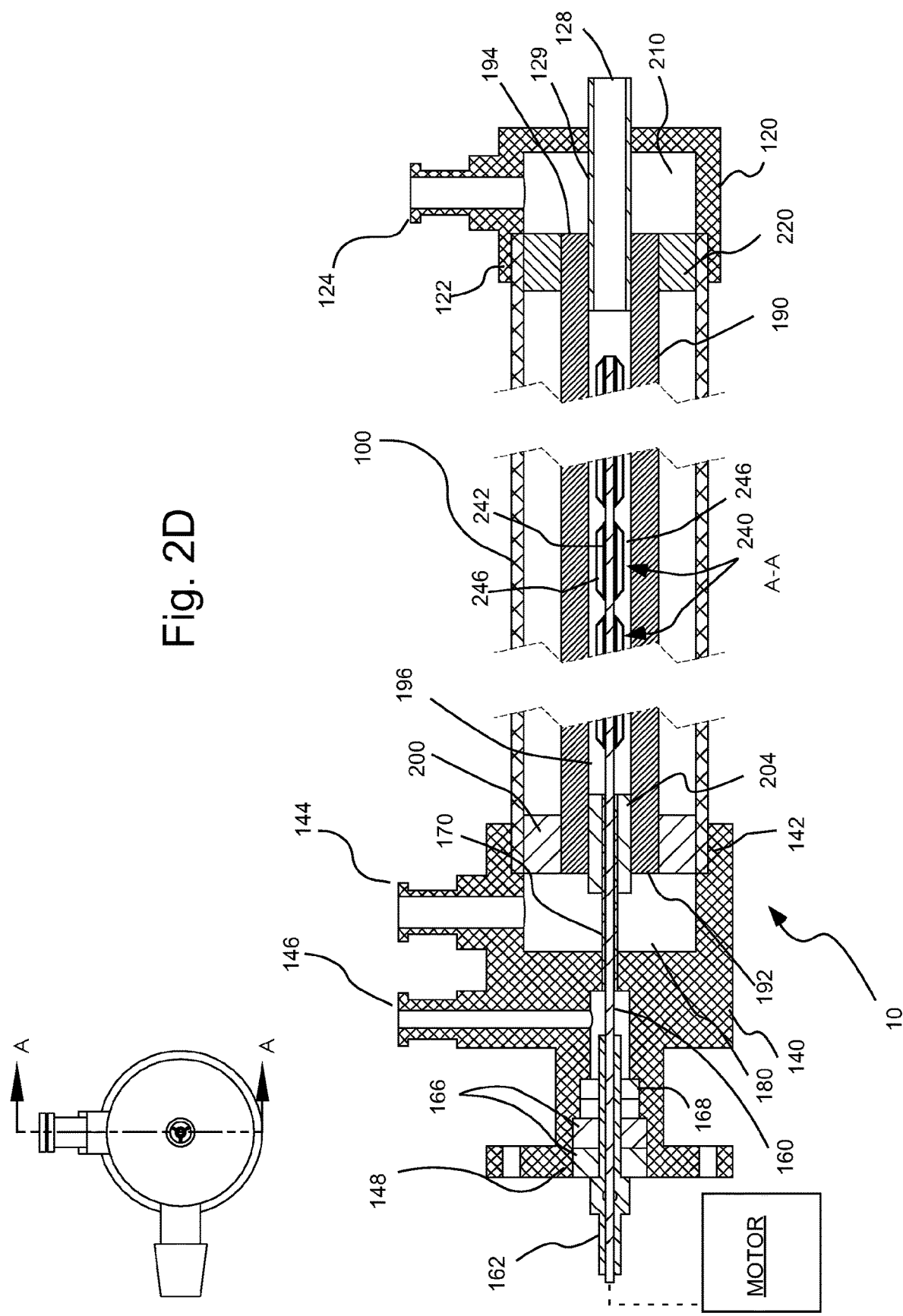
FIG. 2D illustrates a cross-sectional view of the device of FIG. 1A along plane A-A.

In a number of embodiments, second housing end member 140 further includes a seating or coupling 148 to interface with a motor to provide rotation to a drive shaft 160 (as illustrated, for example, in FIG. 2D). Drive shaft 160 may, for example, be formed to be rigid or inflexible (under the conditions of operation of device 10) from, for example, stainless steel. Drive shaft 160 is sufficiently rigid such that, during operation at full speed, the drive shaft 160 does not deflect from the axis of rotation thereof (as a result of centrifugal forces associated with the weight of drives shaft 160 plus all impellers 240 fixed thereto) to a degree to come in contact with any surrounding components of device 10, specifically a surrounding fiber membrane bundle 190. In a number of embodiments, the clearance between impeller(s) 240 and the fiber membranes of hollow fiber membrane bundle 190 in in the range of approximately 0.5 to 3 mm or 0.5 to 2 mm. In the illustrated embodiment, a driveshaft cap 162 surrounding a first end of driveshaft 160 was used to form an operative connection with the motor. Bearings 166, such as ball bearings, may, for example, be seated within coupling 148. In the illustrated embodiment, a seal 168 is also provided in operative connection with drive shaft 160. Saline may be introduced via saline inlet or infusion port 146 to provide continuous flushing of driveshaft 160 and the blood side face of seal 168. A sheath 170 may, for example, be provided around driveshaft 160 to seal the saline infusion pathway from a sweep gas inlet manifold chamber 180. In a number of embodiments, sheath 170 was formed from a lubricious polymer such as polytetrafluoroethylene or PTFE.

Inlet manifold chamber 180 is in fluid connection with sweep gas inlet 144 and an inlet end 192 of an annular shaped hollow fiber bundle 190. In a number of studied embodiments of system 10, a polypropylene hollow fiber bundle 190 such as Celgard® x30-240 available from Membrana GmbH of Wuppertal, Germany was used. In the illustrated embodiment, inlet manifold chamber 180 was formed in second housing end member 140 which was connected to and formed a sealing engagement with housing body 100 via a seating 142 formed therein. Inlet manifold chamber 180 was sealed from the blood flow path of system 10 via a polyurethane fiber potting 200 extending between an inner wall of housing body 100 and an outer surface of hollow fiber bundle 190 and a fiber potting insert 204 extending between an inner surface of hollow fiber bundle 190 and sheath 170. In a number of embodiments, fiber potting insert 204 was machined from stainless steel.

An outlet manifold chamber 210 is in fluid connection with sweep gas outlet 124 and an outlet end 194 of annular-shaped hollow fiber bundle 190. In the illustrated embodiment, outlet manifold chamber 210 was formed in first housing end member 120, which was connected to and formed a sealing engagement with housing body 100 via a seating 122 formed therein. Outlet manifold chamber 210 was sealed from the blood flow path of system 10 via a polyurethane fiber potting 220 extending between an inner wall of housing body 100 and an outer surface of hollow fiber bundle 190 and a blood inlet tube 129 which was sealed against an inner surface of hollow fiber bundle 190. In a number of embodiments, blood inlet tube 129 was formed from stainless steel.

A plurality of impellers 240 (23 in one studied embodiment of system 10) were positioned along the length of rigid drive shaft 160 within interior volume 196 formed by the annular hollow fiber bundle 190. As, for example, illustrated in FIGS. 4A through 4D, impellers 240 included an extending sleeve 242 through which drive shaft 160 passes and a plurality of vanes 246 extending radially outward from sleeve 242. In a number of studied embodiments, impellers 240 included three radially extending vanes. In a number of embodiments, the vanes extended longitudinally along the length of sleeve 242 and extended perpendicular to the axis of sleeve 242. In a number of embodiments, impellers 240 were generally evenly spaced along the length of rigid drive shaft 160.

FIGS. 2A through 2E illustrate cross-sectional views of device 10 via which the flow paths of sweep gas and blood through device 10 are discussed. As, for example, illustrated in FIGS. 2B and 2C, blood enters through an blood inlet port 128 into interior volume 196 formed by annular hollow fiber bundle 190. In other embodiments, blood may, for example enter through the outer gap between annular hollow fiber bundle 190 and housing body 100. Rotation of drive shaft 160, and thereby impellers 240, causes the majority of blood flow to enter a recirculating path through hollow fiber bundle 190 (as represented by dashed arrows in FIG. 2B), starting at the center of each impeller 240. After blood passes through hollow fiber bundle 190 toward the interior wall of housing body 100, the blood flow re-traverses hollow fiber bundle 190 in the opposite direction (that is, radially inward) toward the gap between impellers 240.

The bulk blood flow (illustrated in FIG. 2C) pushes flow gradually toward the blood outlet port 110 at a rate equal to the circuit blood flow rate of the system into which device 10 is incorporated. Once again, blood enters through blood inlet port 128. Most blood recirculates through hollow fiber bundle 190 as illustrated in FIG. 2B, but (as a result of the circuit flow rate), blood moves in a general direction from blood inlet port 128 to blood outlet port 110. Blood can move from inlet to outlet in the impeller region at center, in the fiber bundle (interstitial space between fibers), or the outermost region between the bundle and the housing wall.

Figure 2E:
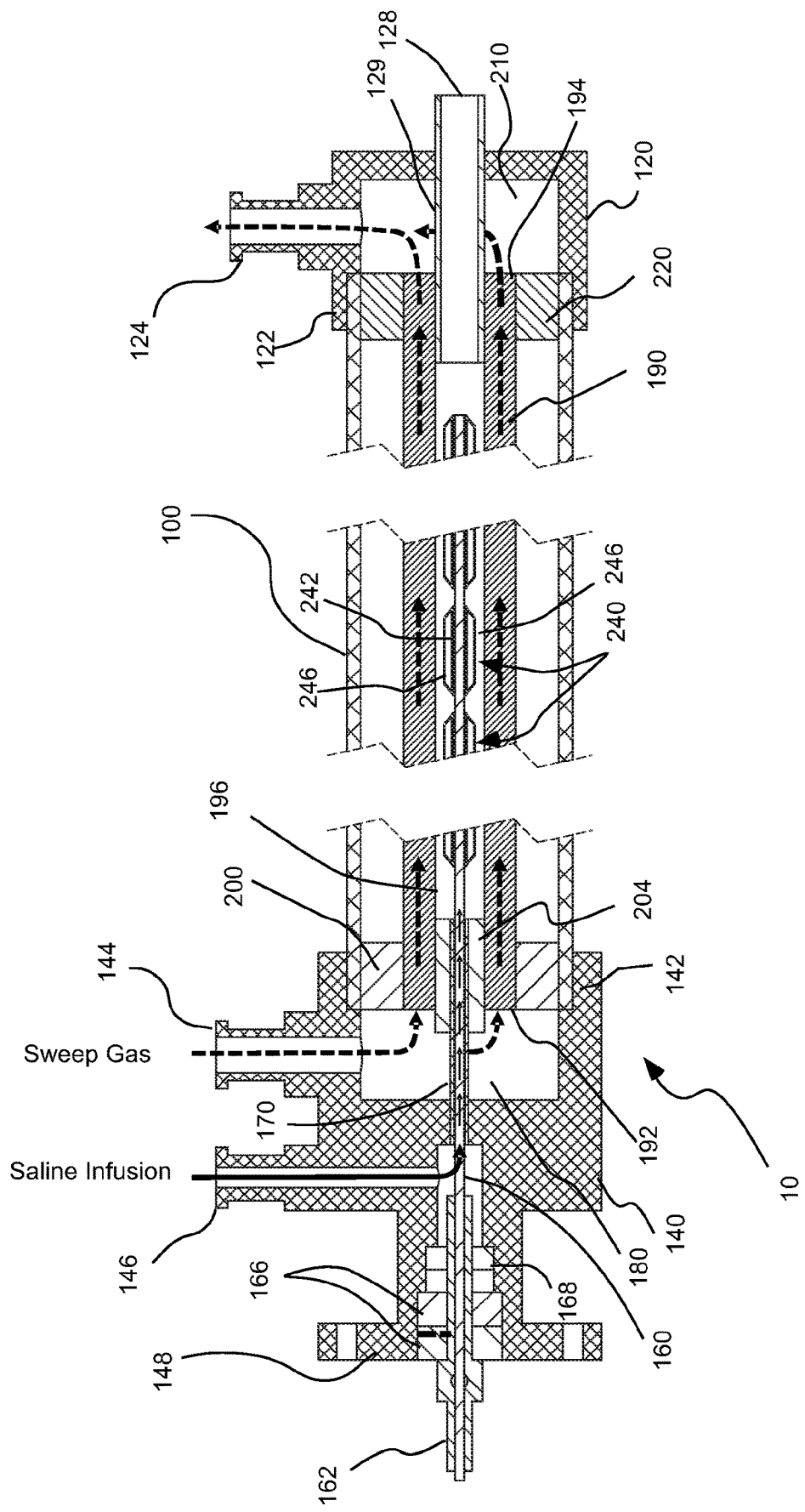
FIG. 2E illustrates a cross-sectional view of the device of FIG. 1A showing bulk flow of sweep gas through the device.
Figure 3A:
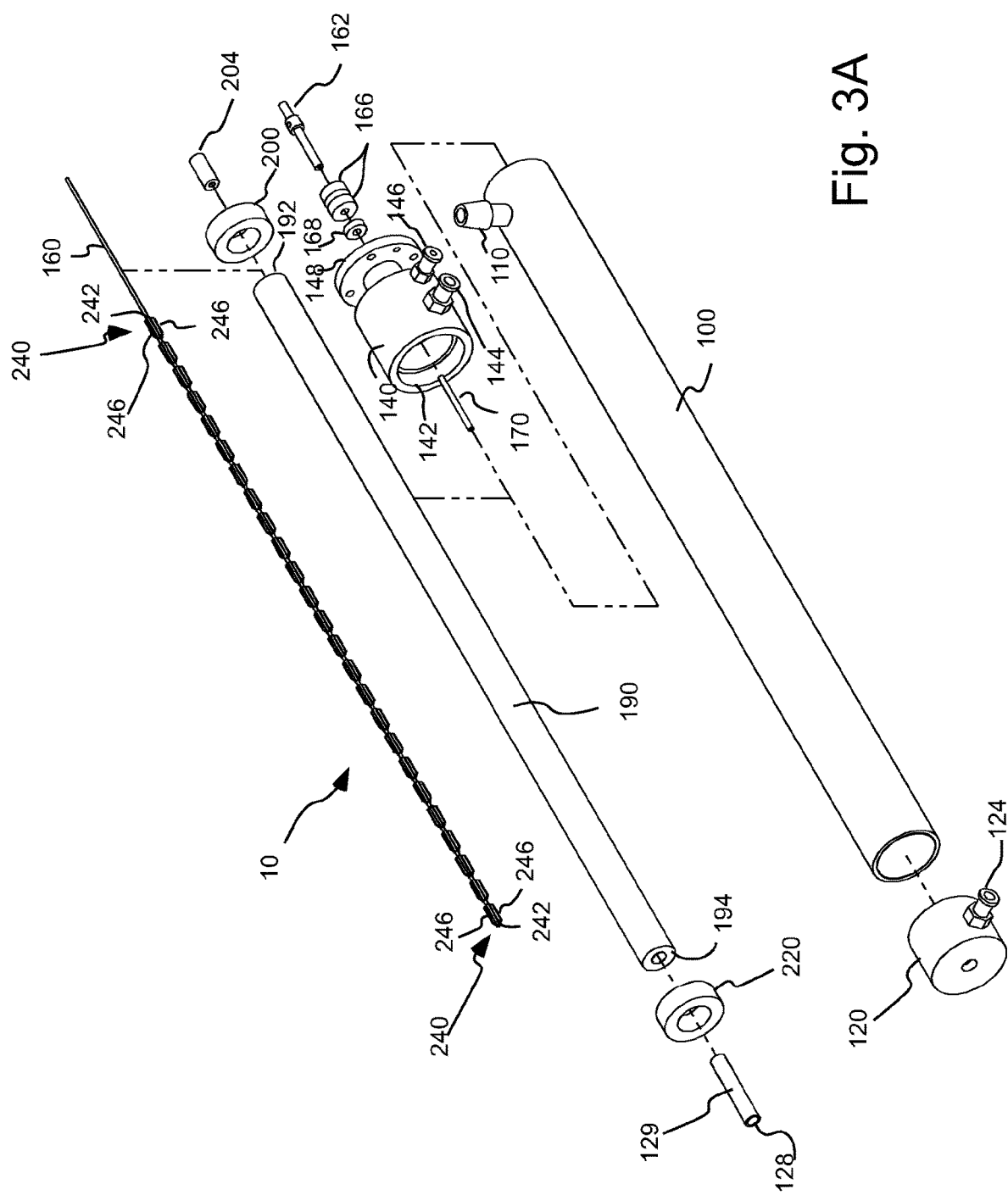
FIG. 3A illustrates a perspective, exploded or disassembled view of the device of FIG. 1A.

As, for example, illustrated in FIG. 2E, sweep gas (represented by dashed arrows) enters sweep gas inlet port 144 and travels to inlet manifold chamber 180 before entering inlet ends 192 of the lumens of hollow fiber bundle lumens 190. As described above, the fibers of hollow fiber bundle 190 are potted concentrically around fiber potting insert 204, sealing the gas pathway from driveshaft 160, which is sheathed inside driveshaft sheath or tubing 170. Sweep gas exits the fiber lumens via outlet ends 194 thereof into outlet manifold chamber 210. Sweep gas exits device 10 through sweep gas outlet port 124.

In the illustrated embodiment, a flushing fluid such as saline (represented by solid arrows in FIG. 2E) is infused through flushing fluid/saline inlet port 146 and travels radially inward toward driveshaft 160. Seal 168 on driveshaft 160 ensures that infused flushing fluid/saline exits through the driveshaft sheath/tubing 170 toward the blood flow path of device 10, rather than leaking through bearings 166.

Another embodiment of a device 10a hereof and components thereof are illustrated in FIGS. 5A through 5D. Similar to device 10, device 10a includes a housing having an extending housing section or body 100a which may, for example, be formed from a polymeric material. A blood outlet port 110a is formed in housing body 100a. A first end member 120a is connected to a first end of housing body 100a. First end member 120a includes a sweep gas outlet port 124a. Unlike device 10, in device 10a, a blood inlet port 128a is formed in housing body 100a rather than first end member 120a. A second housing end member 140a is connected to a second end of housing body 100a. Second housing end member 140a includes a sweep gas inlet port 144a and a saline port 146a.

Similar to device 10, second housing end member 140a includes a seating or coupling 148a to interface with a drive system which may include a motor 500 (illustrated schematically in FIG. 5D) to provide rotation to a drive shaft 160a, which may, for example, be formed to be rigid or inflexible (under the conditions of operation of device 10a) from, for example, stainless steel. As described above, drive shaft 160a is sufficiently rigid such that, during operation at full speed, drive shaft 160a does not deflect from the axis of rotation thereof (as a result of centrifugal forces associated with the weight of drives shaft 160a plus all impellers 240a fixed thereto) to a degree to come in contact with any surrounding components of device 10a (and, specifically, surrounding fiber membrane bundle 190a). As further described above, the clearance between impeller(s) 240a and the fiber membranes of hollow fiber membrane bundle 190a may, for example, be in the range of approximately 0.5 to 3 mm or 0.5 to 2 mm. In the illustrated embodiment of FIGS. 5A through 5D, driveshaft 160a operatively connects directly with the motor without an intervening drive shaft cap. Bearings 166a, such as ball bearings, may, for example, be seated within coupling 148a. A seal 168a and a seal backing 169a (seated between bearings 166a and seal 168a) are provided in operative connection with drive shaft 160a. Seal backing 169a assist in providing a seal between coupling 148a (for, for example, from an acrylic polymer) and shaft 160a. Saline may be introduced via saline inlet or infusion port 146a to provide continuous flushing of driveshaft 160a and the blood side face of seal 168a. In the embodiment of device 10a, a sheath similar to sheath 170 of device 10 was not used. Instead, a potting insert component 204a was machined using the material of sheath 170 (PTFE) or a similar lubricious polymeric or other lubricious sealing material. This embodiment reduces the number of parts in the assembly and improves precision in manufacturing. Sealing contact between driveshaft 160s and potting insert component 204a seals the saline infusion pathway from a sweep gas inlet manifold chamber 180a. In alternative embodiments, the rigid shafts and the operatively connected agitation mechanisms may be driven by a drive systems other than motor. For example, rigid shafts and agitation mechanisms hereof may be magnetically suspended and driven, thereby obviating the need for any bearings and seals As described above, inlet manifold chamber 180a is in fluid connection with sweep gas inlet 144a and an inlet end 192a of an annular shaped hollow fiber bundle 190a. As also described above, a polypropylene hollow fiber bundle 190a such as Celgard® x30-240 available from Membrana GmbH of Wuppertal, Germany may be used. Inlet manifold chamber 180a was formed in second housing end member 140a which was connected to and formed a sealing engagement with housing body 100a via a seating 142a formed therein. Inlet manifold chamber 180a was sealed from the blood flow path of system 10a via a polyurethane fiber potting 200a extending between an inner wall of housing body 100a and an outer surface of hollow fiber bundle 190a and fiber potting insert 204a (machined from PTFE as described above) extending between an inner surface of hollow fiber bundle 190a and drive shaft 160a.

An outlet manifold chamber 210a was provided in fluid connection with sweep gas outlet 124a and an outlet end 194a of annular-shaped hollow fiber bundle 190a. Outlet manifold chamber 210a was formed in first housing end member 120a, which was connected to and formed a sealing engagement with housing body 100a via a seating 122a formed therein. Outlet manifold chamber 210a was sealed from the blood flow path of system 10a via a polyurethane fiber potting 220a extending between an inner wall of housing body 100a and an outer surface of hollow fiber bundle 190a. A solid plug 224a (formed, for example from stainless steel) formed a seal with the inner surface of annular fiber bundle 190a and sealed the blood compartment from gas outlet manifold chamber 210a.

Figure 5A:
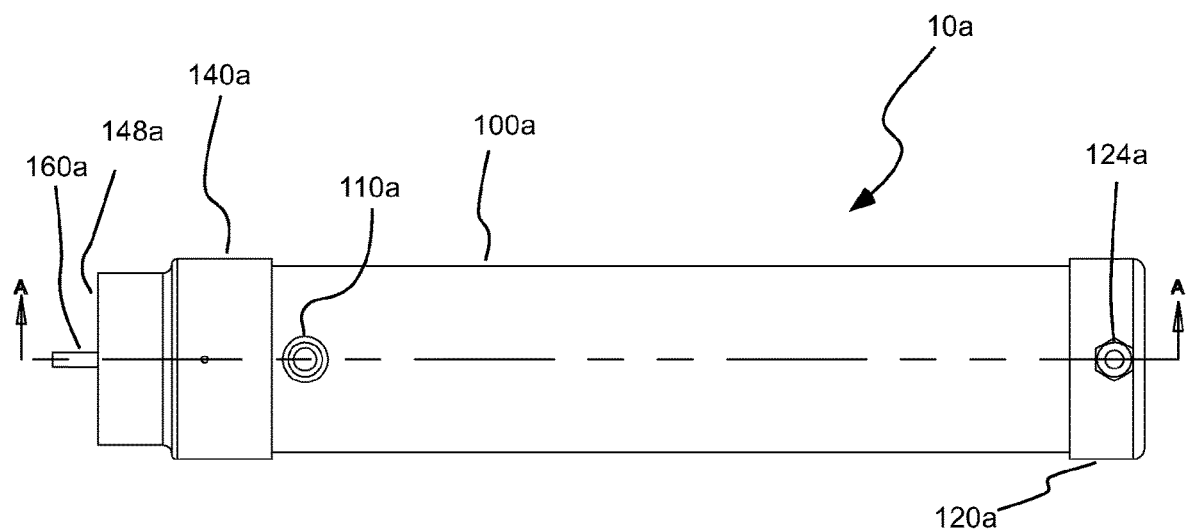
FIG. 5A illustrates a side view of another embodiment of an extracorporeal $CO_2$ removal device hereof.
Figure 5B:
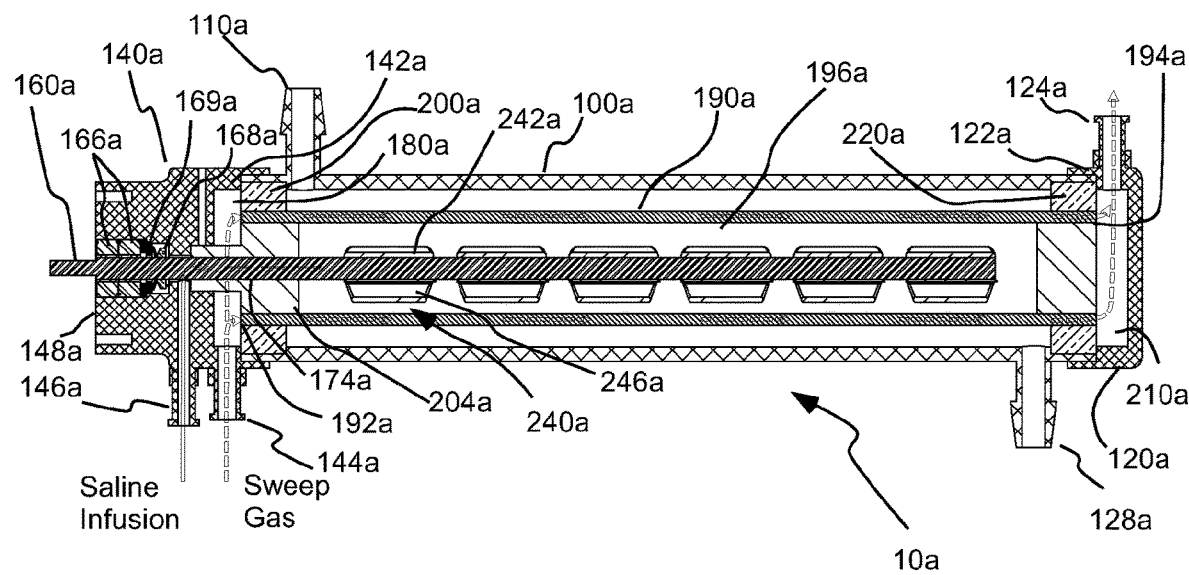
FIG. 5B illustrates a cross-sectional view of the device of FIG. 5A along plane A-A as defined in FIG. 5A, showing idealized flow lines of gas through the device.
Figure 5C:
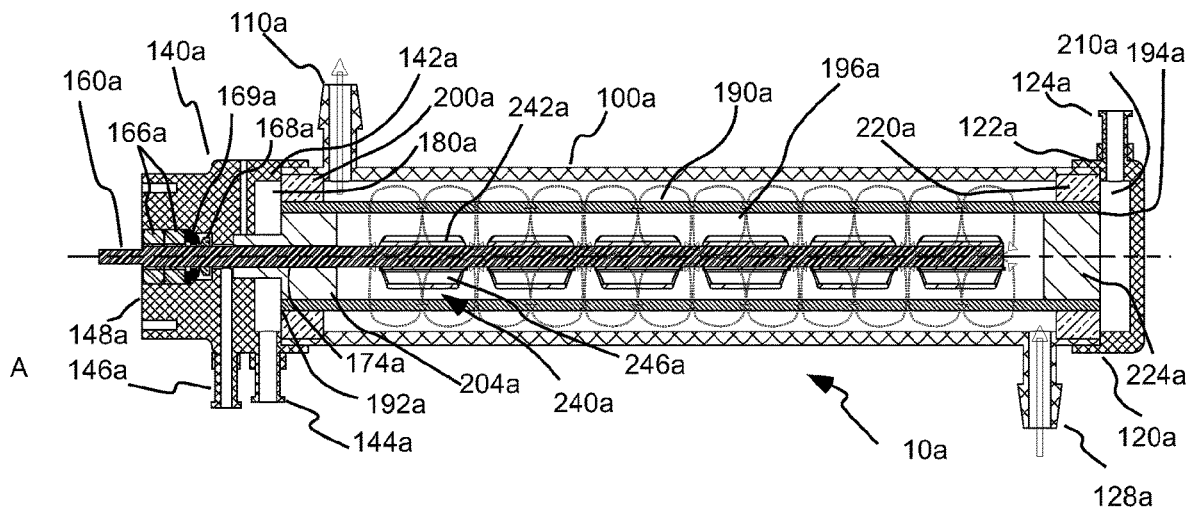
FIG. 5C illustrates a cross-sectional view of the device of FIG. 5A showing idealized flow lines of blood flow through the device and from active mixing induced by impellers.

As described above in connection with device 10, device 10a includes a plurality of impellers 240a (6 in the illustrated embodiment) positioned along the length of rigid drive shaft 160a within interior volume 196a formed by the annular hollow fiber bundle 190a. In a number of embodiments, devices hereof include from 3 to 30 or 3 to 15 impellers. Without limitation to any mechanism, it is desirable to maximize the amount of flow at an angle to (for example, perpendicular to) the direction of bulk flow of blood (that is, in the direction of axis A as illustrated in FIG. 5C) to maximize active mixing. This result may be accomplished by providing a plurality of impellers at spaced positions along shaft 160a.

Figure 5D:
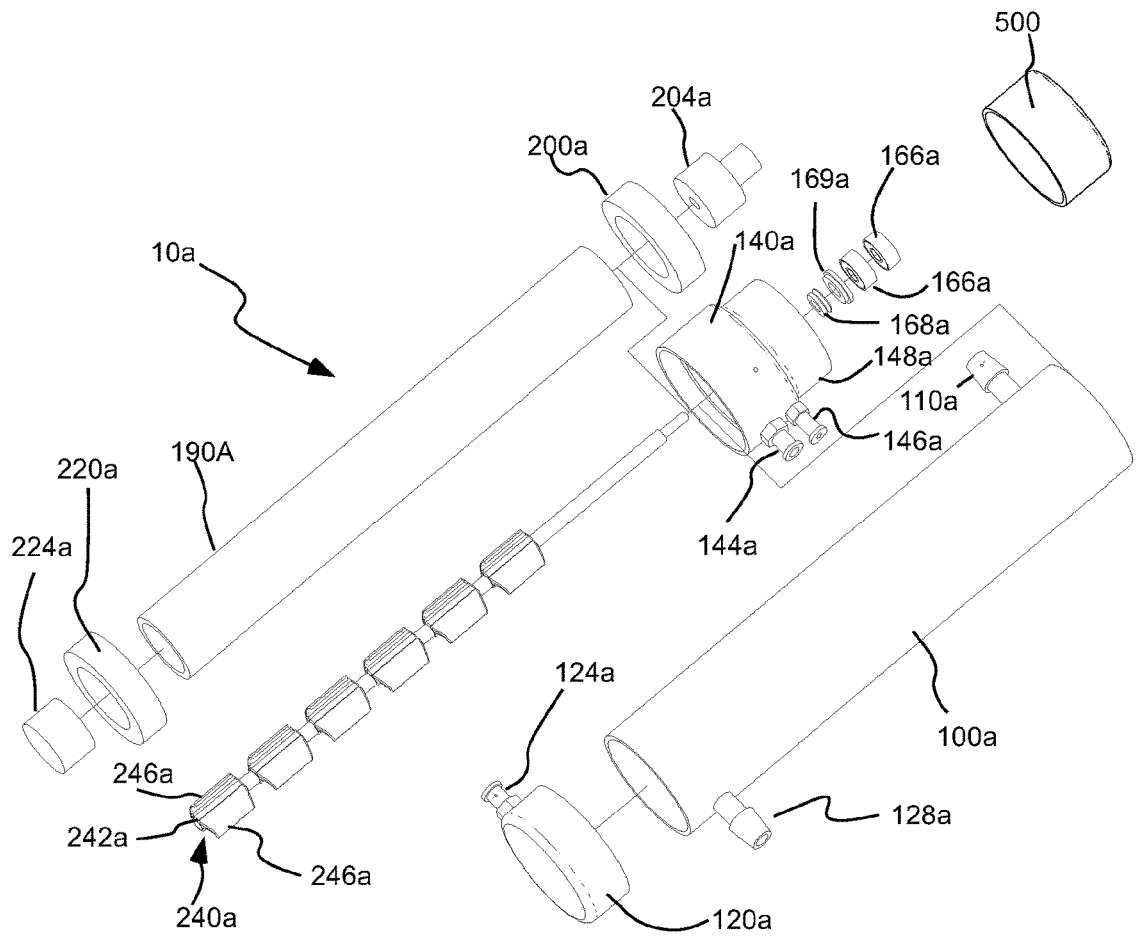
FIG. 5D illustrates a perspective, exploded or disassembled view of the device of FIG. 5A.

Impellers 240a include an extending sleeve 242a through which drive shaft 160a passes and a plurality of vanes 246a extending radially outward from sleeve 242. In the embodiment of device 10a, vanes 246a extended longitudinally along sleeve 242a and were curved as illustrated in FIG. 5D. The curve in vanes 246a acted on the fluid/blood during rotation of vanes 246a around shaft 160a to reorient the fluid flow (that is, pump the fluid/blood) with velocity vectors directed radially outward. In a number of embodiments, impellers 240a were generally evenly spaced along the length of rigid drive shaft 160a.

FIGS. 2A through 2E illustrate cross-sectional views of device 10 via which the flow paths of sweep gas and blood through device 10 are discussed. As, for example, illustrated in FIGS. 2B and 2C, blood enters through an blood inlet port 128 into interior volume 196 formed by annular hollow fiber bundle 190. In other embodiments, blood may, for example enter through the outer gap between annular hollow fiber bundle 190 and housing body 100. Rotation of drive shaft 160, and thereby impellers 240, causes the majority of blood flow to enter a recirculating path through hollow fiber bundle 190 (as represented by dashed arrows in FIG. 2B), starting at the center of each impeller 240. After blood passes through hollow fiber bundle 190 toward the interior wall of housing body 100, the blood flow re-traverses hollow fiber bundle 190 in the opposite direction (that is, radially inward) toward the gap between impellers 240.

Similar to device 10a, the bulk blood flow (illustrated in FIG. 5C) pushes flow gradually toward the blood outlet port 110 at a rate equal to the circuit blood flow rate of the system into which device 10a is incorporated. Blood enters through blood inlet port 128a and recirculates through hollow fiber bundle 190a. As a result of the circuit flow rate, blood moves in a general direction from blood inlet port 128a to blood outlet port 110a. Sweep gas (represented by dashed arrows in FIG. 5B) enters sweep gas inlet port 144a and travels to inlet manifold chamber 180a to inlet ends 192a of the lumens of hollow fiber bundle lumens 190a. Sweep gas exits the fiber lumens via outlet ends 194a into outlet manifold chamber 210a and exits device 10a through sweep gas outlet port 124a.

In a design configuration such as device 10a wherein the blood flow is introduced within the housing into a space of volume between fiber bundle 190a and an inner wall of housing body 100a, gas exchange was found to approximately equivalent to gas exchange in a similarly device such as device 10, wherein blood is introduced within a volume defined by the annular fiber bundle 190, at higher rotation speeds, but slightly lower at very low rotation speeds. Relocating blood inlet port 128a to housing body 100a in device 10a facilitate manufacture as compared to blood inlet port 128 of device 10. At higher rotation speeds typically used in devices hereof, the agitation generated by impellers 240a is significant enough that the location of blood inlet port 128a minimally affects resulting performance as compared to blood inlet port 128 of device 10.

Figure 6A:
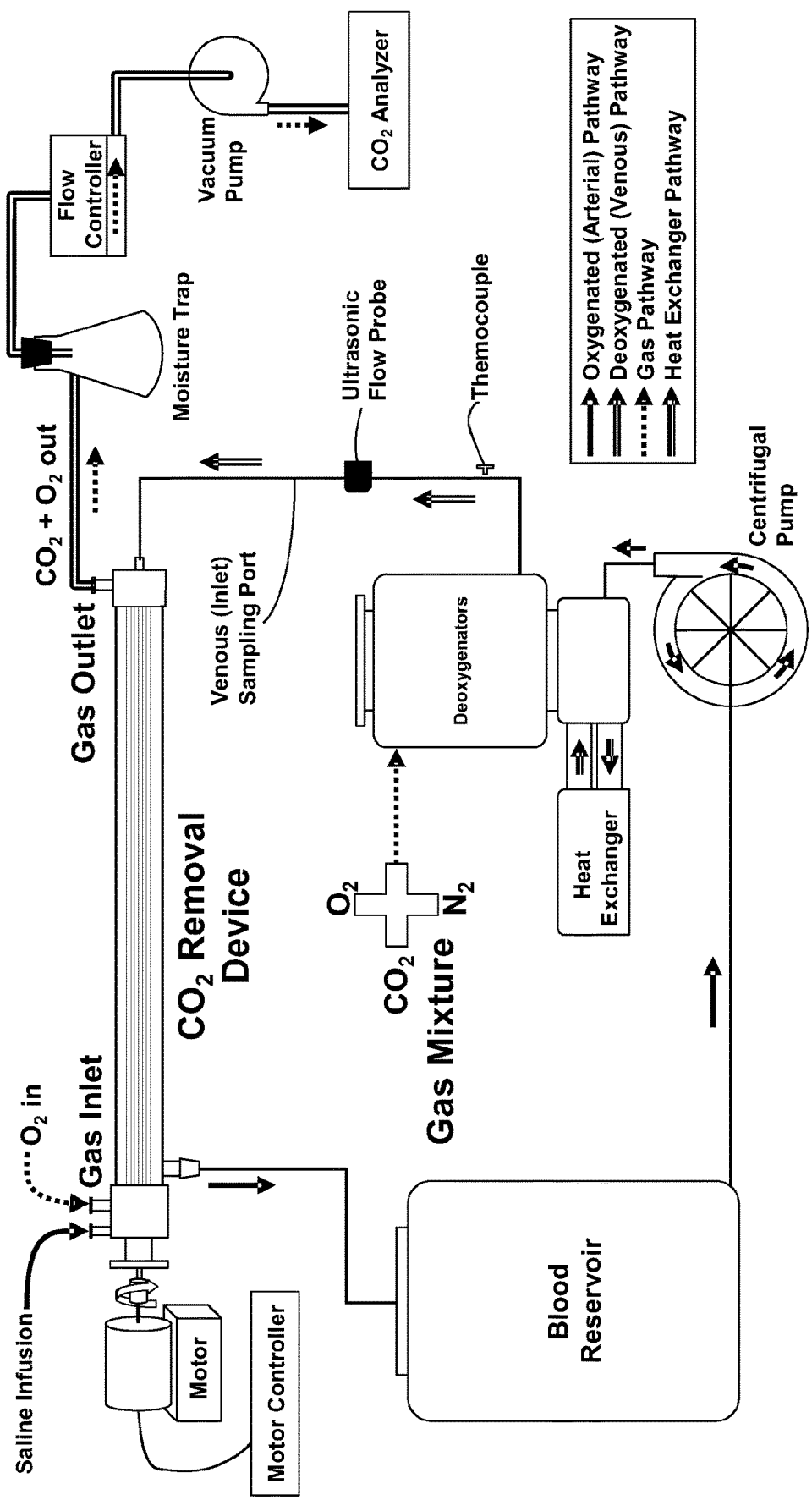
FIG. 6A illustrates an in vitro blood flow circuit used for gas exchange testing of a number of devices hereof.
Figure 6B:
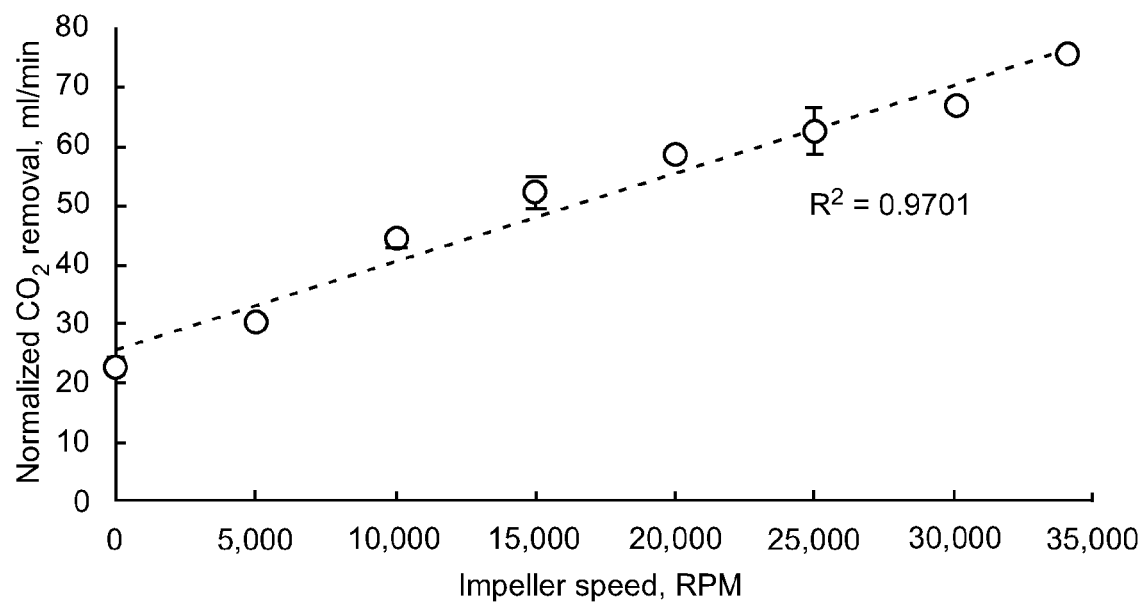
FIG. 6B illustrates a graph of measured $CO_2$ removal rate as a function of impeller rotation rate in studies of a $CO_2$ removal devices hereof using the in vitro blood flow circuit of FIG. 6A at a flow rate of 250 mL/min.

In a number of studies of devices and systems hereof, gas exchange performance was evaluated in an in vitro flow loop, system or circuit illustrated in FIG. 6A. In a number of studies, the inlet blood gas tensions were maintained at $pCO_2=45\pm5$ mmHg and $sO_2=65\pm5\%$ using commercially available oxygenators (Deoxyginators) and an $O_2/CO_2/N_2$ gas mixture. Circulating blood was maintained constant at 250 ml/min with a commercially available blood pump and tubing clamp, as verified by an on-line ultrasonic flow probe. Pure $O_2$ sweep gas was pulled through the fibers of the hollow fiber bundle (counter-current to the blood flow) at a flow rate of 6.2 L/min. The percent $CO_2$ in the exiting sweep gas was measured and used to calculate a $CO_2$ removal rate. Evidence of active mixing was demonstrated by experimental comparison of the achieved $CO_2$ removal rate versus impeller rotation speed as set forth in FIG. 5B. In a number of studied embodiments, the impeller rotation speed was in the range of 500-35,000 RPM, approximately 10,000-35000 RPM, or approximately 30,000-34,000 RPM In a number of other embodiments, the impeller rotation speed may, for example, be in the range of approximately 500-10,000 RPM, approximately, 2000-8000 RPM, or approximately 5500-6500 RPM. Even at relatively high impeller rotational speeds, the impellers contribute little (for example, less than 5%, less than 2% or less than 1%) or zero to the bulk flow rate through the devices and systems hereof, providing for control of active mixing that is substantially independent or independent of control of bulk flow. At a blood flow rate of 250 ml/min, measured $CO_2$ removal increased 229% at the highest rotation speed. Inlet $pCO_2$ was verified to equal 45±5 mmHg prior to each measurement in the studies of FIG. 6B. Removal rates were normalized to an inlet $pCO_2$ of 45 mm Hg.

In the studies hereof, device 10 measured approximately 35-40 cm in length (wherein, the blood-primed portion was approximately 30 cm in length. Device 10a was approximately 20 to 25 cm in length and the blood-primed portion was approximately 17 cm in length. Device 10 had a diameter in the range of 2.5 to 4 cm (wherein the blood primed portion had a diameter of approximately 2.22 cm), while device 10a had a diameter in the range of 4.45 cm (wherein the blood primed portion had a diameter of approximately 4.13 cm). The priming volume of the studied device 10 was approximately 100 mL, while the priming volume of device 10a was approximately 150 mL. The number of fiber membranes (0.03 cm diameter, polypropylene fibers) of studied device 10a was 750, and 23 impellers were fixed on drive shaft 160. The number of fiber membranes (0.03 cm diameter, polypropylene fibers) of studied device 10a was 1331, and 6 impellers were fixed on drive shaft 160a. Alternative device dimensions with various aspect ratios (length versus fiber bundle diameter) may yield similar gas exchange performance. In a number of embodiments, devices hereof may, for example, have blood primed regions in the range of 10-30 cm in length, have diameters in the range of 2.22-5 cm, and/or have priming volumes in the range of 75-150 mL. In a number of embodiments hereof, devices hereof may, for example, include 750-4000 hollow fiber membranes, and/or include 1-30, 3-30 or 3-15 impellers 240 on drive shaft 160.

Figure 7:
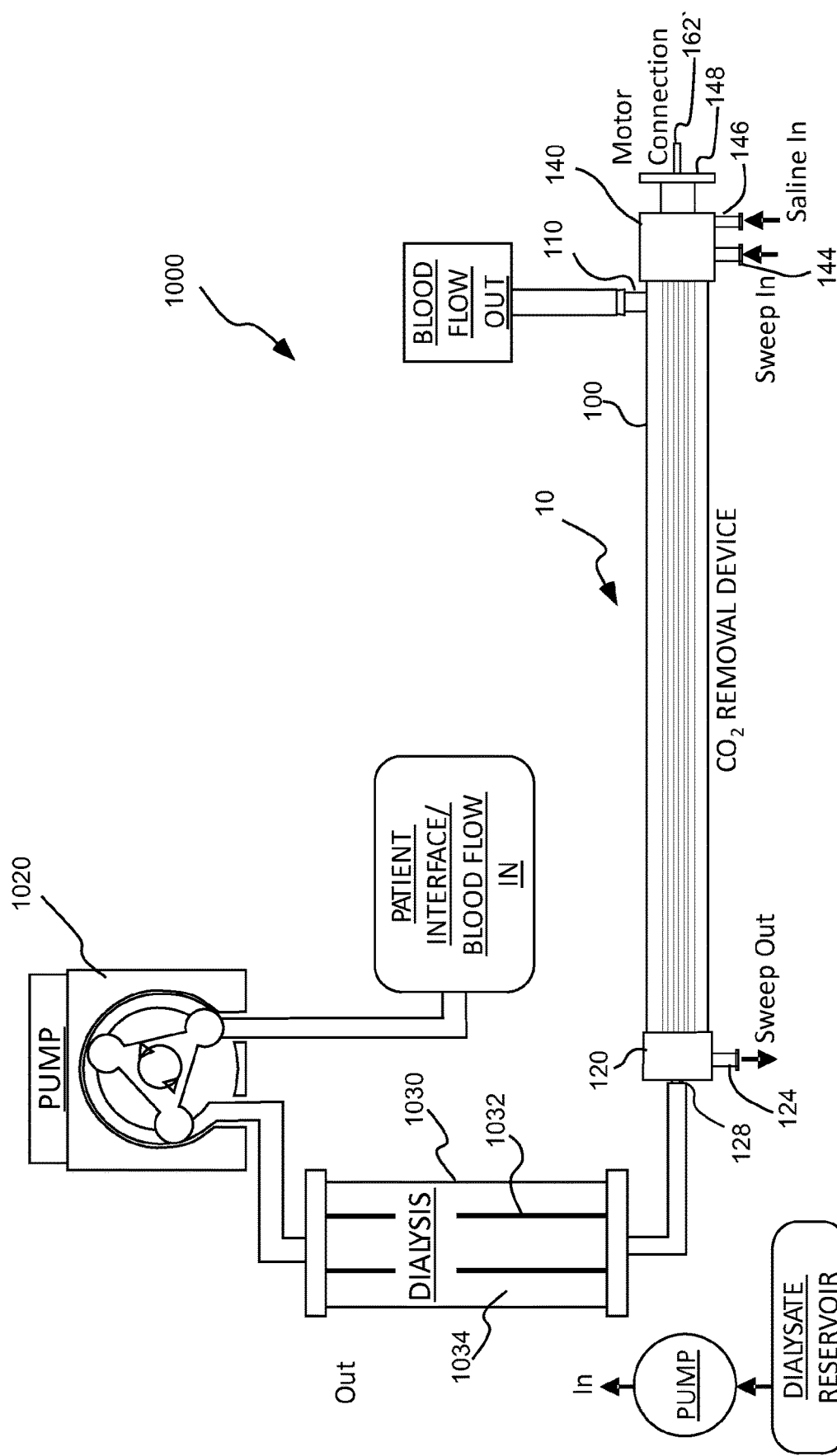
FIG. 7 illustrated a schematic representation $CO_2$ removal device hereof in fluid connection with a renal dialysis device.

FIG. 7 illustrates a representative example of a system 1000 for reducing the concentration of $CO_2$ in blood plasma and effecting renal dialysis. Oxygenation of blood plasma can be effected using a sweep gas including (or consisting of) oxygen. In the case of $CO_2$ removal, the sweep gas supply includes a lower concentration of $CO_2$ than present in the blood plasma, giving rise to a concentration gradient/driving force across the membranes of the hollow fibers. Typically, the sweep gas supply will include no or substantially no $CO_2$ therein to maximize the driving force. System 1000 includes patient interfaces for removal of blood from the patient and return of filtered blood to the patient and system 10 for removal of $CO_2$/oxygenation as described above. One or more blood pumps 1020 as known in the art may be used for effecting flow of blood through system 1000 as required. A dialyzer or dialysis filter system 1030 may, for example, include a plurality of, semipermeable fibers 1032. In dialysis filter system 1030, the blood may, for example, flow through semi-permeable fibers 1032 and the dialysate flows in a volume 1034 around fibers 1032. After passing through dialysis filter system 1030, the filtered blood is returned to the patient. As described above, blood flow rates currently used in dialysis systems can be used in system 1000 (typically, approximately 250 mL/min). For example, the blood flow rate may be in the range of approximately 200 to approximately 500 mL/min, in the range of approximately 200 to 400 mL/min, or in the range of approximately 225 to 275 mL/min. The order of circuit components in the systems hereof can be varied. In system 1000, of FIG. 6, for example, $CO_2$ removal device 10 receives flow after both pump 1020 and dialysis filter system 1030. Device 10 could, for example, also be placed between pump 1020 and dialysis filter system 1030. Typically, device 10 is placed after a pump in the systems hereof to provide a positive fluid pressure (to reduce or eliminate the risk of pulling gas out of the fibers into the blood pathway).

In a manner similar to that described in connection with oxygenators or lung assist systems in U.S. Pat. Nos. 7,763,097 and 8,043,411, the disclosure of which are incorporated herein by reference, carbonic anhydrase or CA may be used on or in the vicinity of the fibers of hollow fiber membrane 190 of device 10 to drive or increase the removal of bicarbonate from blood. CA reversibly catalyzes hydration of $CO_2$ into carbonic acid, which then rapidly dissociates into bicarbonate ion. Immobilized CA may, for example, be used to facilitate diffusion toward a membrane including the immobilized enzyme. CA immobilized on or in the vicinity of the surface of the fibers of hollow fiber membrane 190 enables "facilitated diffusion" of $CO_2$ as bicarbonate towards the fibers of hollow fiber membrane 190 and enhances the removal rate of $CO_2$. Indeed, creating velocity streams across the orientation of the fiber membranes may increase the effectiveness of CA. In that regard, in passive test devices (without active mixing) the enhancement of gas exchange by carbonic anhydrase and blood has been found to be limited by the diffusional boundary layer and not by the amount or kinetics of the carbonic anhydrase.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. An extracorporeal gas exchange device, comprising: a housing, a rigid shaft rotatable within the housing, a plurality of agitation mechanisms positioned on the rigid shaft, and a plurality of hollow gas permeable fibers adapted to permit diffusion of gas between fluid flowing within the housing and an interior of the plurality of gas permeable hollow fibers, the plurality of hollow gas permeable fibers being positioned radially outward from the plurality of agitation mechanisms, the rotational speed of the rigid shaft being adjustable independent of the flow rate of fluid through the housing.

2. The extracorporeal gas exchange device of claim 1 wherein the housing comprises a sweep gas inlet in fluid connection with an inlet end of the plurality of hollow gas permeable fibers, a sweep gas outlet in fluid connection with an outlet end of the plurality of hollow gas permeable fibers, a fluid inlet, and a fluid outlet, the fluid inlet and the fluid outlet being isolated from fluid connection with the sweep gas inlet and the sweep gas outlet.

3. The extracorporeal gas exchange device of claim 2 comprising between 3 and 30 agitation mechanisms positioned on the rigid shaft.

4. The extracorporeal gas exchange device of claim 2 comprising between 3 and 15 agitation mechanisms positioned on the rigid shaft.

5. The extracorporeal gas exchange device of claim 3 wherein the plurality of agitation mechanisms comprise a plurality of impellers in spaced positions on the rigid shaft.

6. The extracorporeal gas exchange device of claim 5 wherein the plurality of impellers are generally evenly spaced on the rigid shaft.

7. The extracorporeal gas exchange device of claim 5 wherein each of the plurality of impellers comprise curved vanes.

8. The extracorporeal gas exchange device of claim 6 wherein the fluid inlet is adapted to be placed in fluid connection with a patient and the fluid is blood.

9. The extracorporeal gas exchange device of claim 8 wherein a sweep gas placed in fluid connection with the sweep gas inlet is adapted to remove carbon dioxide from the blood.

10. The extracorporeal gas exchange device of claim 9 wherein the sweep gas comprises oxygen.

11. The extracorporeal gas exchange device of claim 10 wherein the flow rate of blood through the housing is in the range of 200 to 500 mL/min.

12. The extracorporeal gas exchange device of claim 10 wherein the flow rate of blood through the housing is in the range of 200 to 400 mL/min.

13. The extracorporeal gas exchange device of claim 1 wherein the plurality of agitation mechanisms are adjacent the plurality of hollow gas permeable fibers without an intervening component.

14. A system, comprising:
at least one pump device adapted to effect fluid flow;
at least one dialysis system in fluid connection with the at least one pump device; and
at least one extracorporeal gas exchanged device in fluid connection with the at least one pump device and the at least one dialysis system, the extracorporeal gas exchange device comprising a housing, a rigid shaft rotatable within the housing, a plurality of agitation mechanisms positioned on the rigid shaft, and a plurality of hollow gas permeable fibers adapted to permit diffusion of gas between fluid flowing within the housing and an interior of the hollow fibers, the plurality of hollow gas permeable fibers being positioned radially outward from the plurality of agitation mechanisms, the rotational speed of the rigid shaft being adjustable independent of the rate of fluid flow through the housing.

15. An extracorporeal gas exchange device, comprising:
a housing, a rigid shaft rotatable within the housing, a plurality of agitation mechanisms positioned on the rigid shaft, and a plurality of hollow gas permeable fibers adapted to permit diffusion of gas between fluid flowing within the housing and an interior of the plurality of hollow gas permeable fibers, the plurality of hollow gas permeable fibers being positioned radially outward from the plurality of agitation mechanisms.

16. The extracorporeal gas exchange device of claim 15 wherein the plurality of agitation mechanisms are adjacent the plurality of hollow gas permeable fibers without an intervening component.

17. The extracorporeal gas exchange device of claim 15 wherein the rotational speed of the rigid shaft is adjustable independent of the flow rate of fluid through the housing.

18. An extracorporeal gas exchange device, comprising:
a housing, a shaft rotatable within the housing, a plurality of agitation mechanisms positioned on the shaft, and a plurality of hollow gas permeable fibers adapted to permit diffusion of gas between fluid flowing within the housing and an interior of the plurality of hollow gas permeable fibers, the plurality of hollow gas permeable fibers being positioned radially outward from the plurality of agitation mechanisms, the rotational speed of the shaft being adjustable independent of the flow rate of fluid through the housing.

* * * * *

UNITED STATES PATENT AND TRADEMARK OFFICE
CERTIFICATE OF CORRECTION

PATENT NO. : 10,549,022 B2
APPLICATION NO. : 15/542532
DATED : February 4, 2020
INVENTOR(S) : Richard Garrett Jeffries, William J. Federspiel and Brian Joseph Frankowski Page 1 of 1

It is certified that error appears in the above-identified patent and that said Letters Patent is hereby corrected as shown below:

In the Specification

Column 1, Line 7, before the word "claims" insert -- is a national phase filing of PCT International Patent Application No. PCT/US2016/014029, filed January 20, 2016, which --.
Column 1, Line 9, delete "disclosure of which is" and insert -- disclosures of which are --.

Signed and Sealed this
Thirtieth Day of June, 2020

Andrei Iancu
*Director of the United States Patent and Trademark Office*